US012714502B2

(12) United States Patent
Straub et al.

(10) Patent No.: US 12,714,502 B2
(45) Date of Patent: Aug. 25, 2026

(54) METHOD AND SYSTEM FOR CUSTOMIZING TRAINING OF A USER TO PERFORM PERCUTANEOUS CORONARY INTERVENTIONS

(71) Applicant: CAE HEALTHCARE CANADA INC., Saint-Laurent (CA)

(72) Inventors: Randall Straub, Saint-Laurent (CA); Jordan Bano, Saint-Laurent (CA); Michael Cloutier, Saint-Laurent (CA); Clement Forest, Saint-Laurent (CA); Peter Haddad, Saint-Laurent (CA); Ivona Sosic, Saint-Laurent (CA); Guillaume Normandin, Saint-Laurent (CA)

(73) Assignee: CAE HEALTHCARE CANADA INC., Saint-Laurent (CA)

( * ) Notice: Subject to any disclaimer, the term of this patent is extended or adjusted under 35 U.S.C. 154(b) by 598 days.

(21) Appl. No.: 18/187,879

(22) Filed: Mar. 22, 2023

(65) Prior Publication Data

US 2023/0301721 A1 Sep. 28, 2023

Related U.S. Application Data

(60) Provisional application No. 63/269,810, filed on Mar. 23, 2022.

(51) Int. Cl.

*A61B 34/10* (2016.01)
*A61B 5/02* (2006.01)
*G16H 50/50* (2018.01)

(52) U.S. Cl.

CPC .......... *A61B 34/10* (2016.02); *A61B 5/02007* (2013.01); *G16H 50/50* (2018.01)

(58) Field of Classification Search

CPC ..... A61B 34/10; A61B 5/02007; A61B 34/25; G16H 50/50; G16H 20/40; G09B 23/285; G09B 23/288

See application file for complete search history.

(56) References Cited

U.S. PATENT DOCUMENTS

2004/0033477 A1* 2/2004 Ramphal ............. G09B 23/306 434/272
2007/0275359 A1 11/2007 Rotnes et al.
(Continued)

FOREIGN PATENT DOCUMENTS

CN 21218176 12/2020

OTHER PUBLICATIONS

"Carotid Intervention Procedural Training Module." VIST Brochure. Mentice, 2013. (Year: 2013).*
(Continued)

*Primary Examiner* — John R Wallace
(74) *Attorney, Agent, or Firm* — FASKEN MARTINEAU DUMOULIN LLP; Johann Gest; Serge Lapointe

(57) ABSTRACT

There is described a computer-implemented method for creating a training scenario to perform a percutaneous coronary intervention using an elongated instrument and a patient simulator, the computer-implemented method comprising: receiving a desired position for a lesion; receiving a desired value for at least one property of the lesion; configuring a haptic feedback to be applied on the elongated instrument when received in the patient simulator based on the desired location for the lesion and the desired value for the properties of the lesion, the haptic feedback; and outputting the haptic feedback, the desired position and the desired value for the properties.

20 Claims, 11 Drawing Sheets

(56) References Cited

U.S. PATENT DOCUMENTS

2014/0272865 A1 9/2014 Kim
2020/0005677 A1 1/2020 Gulasy et al.
2021/0369394 A1* 12/2021 Braido .................. G16H 20/40

OTHER PUBLICATIONS

Li, Shuai et al. "Design and Evaluation of Personalized Percutaneous Coronary Intervention Surgery Simulation System." IEEE transactions on visualization and computer graphics 27.11 (2021): Web. (Year: 2021).*
Wu, J. et al., "A Preliminary Real-Time and Realistic Simulation Environment for Percutaneous Coronary Intervention". BioMed research international, Mar. 23, 2015 (Mar. 23, 2015), 10 pgs. in total, ISSN http://dx.doi.org/10.l155/2015/183157 [online] [retrieved on Jun. 2, 2023 (Jun. 2, 2023)]. Retrieved from the Internet: <https://www.hindawi.com/journals/bmri/2015/183157/>.
Wu, J. et al., "A Computer-Based Simulator for Percutaneous Coronary Intervention". International Journal of Life Sciences Biotechnology and Pharma Research, Apr. 1, 2015 (Apr. 1, 2015), vol. vol. 4, Issue No. 2, pp. 113-116, [online] [retrieved on Jun. 2, 2023 (Jun. 2, 2023)]. Retrieved from the Internet: <https://scholar.archive.org/work/ogva6q2injhjnipnsy7qcrmobm/access/way back/http://www.ijlbpr.com/papers/18-HOO14.pdf>.
Tai, Y. et al., "A High-Immersive Medical Training Platform Using Direct Intraoperative Data". IEEE access, Oct. 31, 2018 (Oct. 31, 2018), vol. 6, pp. 69438-69452, ISSN doi: 10.1 109/ACCESS.2018.2877732 [online] [retrieved on Jun. 2, 2023 (Jun. 2, 2023)]. Retrieved from the Internet: <https://ieeexplore.ieee.org/iel7/6287639/6514899/0851 6286.pdf> (see Abstract; Section I—Introduction; Section II—Related Works; Section III—Materials and Methods; Section •• Discussion and Section VI—Conclusion, along with figs. 3 and 10).
Bandari, N. M. et al., "Hybrid piezoresistive-optical tactile sensor for simultaneous measurement of tissue stiffness and detection of tissue discontinuity". Journal of biomedical optics, Jul. 1, 2017 (Jul. 1, 2017), vol. vol. 22, Issue No. 7, pp. 077002-0-077002-10, ISSN doi:10.ll 1 7/1.JBO.22.7.077002 [online] [retrieved on Jun. 2, 2023 (Jun. 2, 2023)]. Retrieved from the Internet:<https://www.spiedigitallibrary.org/joumalArticle/Download?fullDOI=10.1117/1.JBO.22.7.077002>.
Hao, A. et al., "Personalized cardiovascular intervention simulation system". Virtual Reality & Intelligent Hardware, Apr. 1, 2020 (Apr. 1, 2020), vol. vol. 2, Issue No. 2, pp. 104-118, ISSN DOI: 10.1016/j.vrih.2020.04.001 [online] [retrieved on Jun. 2, 2023 (Jun. 2, 2023)]. Retrieved from the Internet: <https://www.sciencedirect.com/science/article/pii/S20965796203001 52/pdf?md5=12bfdfl23742c24ae89359b0e838c5eb&pid=1-s2.0-S2096579620300152-main.pdf>.
Trehan, K. et al., "Simulation in cardiothoracic surgical training: Where do we stand?". The Journal of thoracic and cardiovascular surgery, Jan. 1, 2014 (Jan. 1, 2014), vol. vol. 147, Issue No. 1, pp. 18-24, ISSN http://dx.doi.org/10.1016/j.jtcvs.2013.09.007 [online] [retrieved on Jun. 2, 2023 (Jun. 2, 2023)]. Retrieved from the Internet: <https://www.sciencedirect.com/science/article/pii/S0022522313010775>.
Wei, P. et al., "FEM-based Guide Wire Simulation and Interaction for a Minimally Invasive Vascular Surgery Training System". Proceeding of the 11th World Congress on Intelligent Control and Automation, IEEE, Jun. 29, 2014, pp. 964-969) [online] [retrieved on Jun. 2, 2023 (Jun. 2, 2023)]. Retrieved from the Internet: <https://ieeexplore.ieee.org/iel7/7043694/7052676/07052846.pdf>.

* cited by examiner

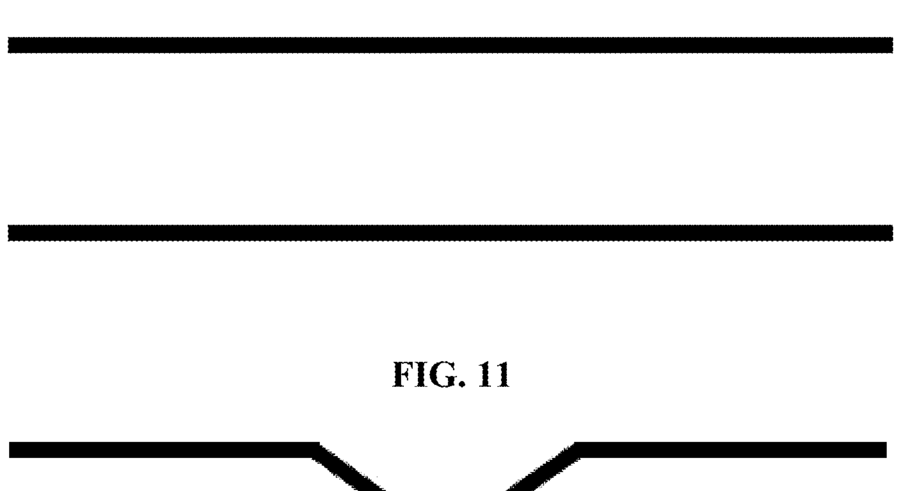
FIG. 11
FIG. 12
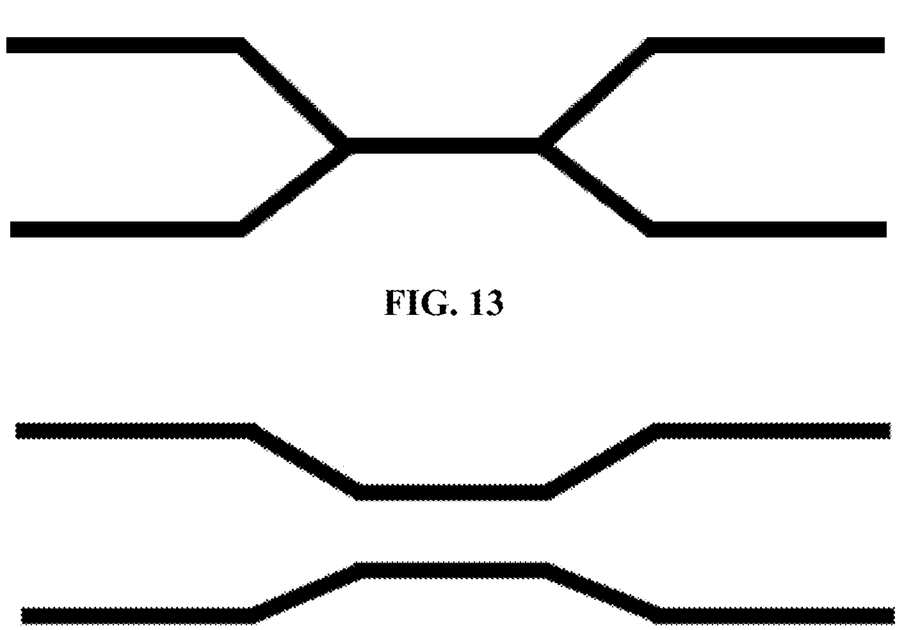
FIG. 13
FIG. 14

METHOD AND SYSTEM FOR CUSTOMIZING TRAINING OF A USER TO PERFORM PERCUTANEOUS CORONARY INTERVENTIONS

CROSS-REFERENCE TO RELATED APPLICATION

The present application claims priority on U.S. Provisional Patent Application No. 63/269,810 filed on Mar. 23, 2022.

FIELD

The present technology pertains to the field of methods and system for training healthcare professionals to perform percutaneous coronary interventions using an elongated medical instrument, and more particularly to methods and systems that allow customizing training scenarios or cases.

BACKGROUND

Systems for training healthcare professionals to perform percutaneous coronary interventions usually comprise a patient simulator in which elongated medical instruments such as wires and catheters are inserted to treat a lesion present in a blood vessel, and a computer for generating simulated images of the intervention to guide the healthcare professional while training. Simulation scenarios or cases have historically been created by simulation companies during the design process to present the healthcare professionals to be trained with different types of lesions such as lesions having different locations, shapes and/or sizes.

At least some of the current training systems include extensive libraries of individual training cases that have fixed learning experiences. While effective, it creates an environment where instructors may be intimidated by the extensive libraries of individual training cases, leading the instructors to use only a few training cases amongst the extensive libraries.

Furthermore, at least some of the current training systems are configured to launch training cases that already describe the vessel to be treated, thereby reducing the effectiveness of the normal diagnostic phase to be performed by a healthcare professional prior to any procedure.

Therefore, there is a need for an improved method and system for customizing the training of healthcare professionals to perform percutaneous coronary interventions using an elongated medical instrument.

SUMMARY

It is an object of the present technology to provide instructors with the ability to create a customized training experience by allowing them to choose between a predefined number of different locations for a lesion and inputting desired values for at least some characteristics or properties of the lesion.

According to a first broad aspect, there is provided a computer-implemented method for creating a training scenario to perform a percutaneous coronary intervention using an elongated instrument and a patient simulator, the computer-implemented method comprising: receiving a desired position for a lesion; receiving a desired value for at least one property of the lesion; configuring a haptic feedback to be applied on the elongated instrument when received in the patient simulator based on the desired location for the lesion and the desired value for the properties of the lesion, the haptic feedback; and outputting the haptic feedback, the desired position and the desired value for the properties.

In one embodiment, the step of receiving the desired position comprises receiving a selection of the desired position amongst a predefined number of possible lesion positions.

In one embodiment, the at least one property of the lesion comprises at least one of a length of the lesion, an occlusion percentage, a Thrombolysis In Myocardial Infarction (TIMI) flow grade and an eccentricity of the lesion.

In one embodiment, the method further comprises generating a patient description based on the desired position for the lesion and the desired value for the at least one property of the lesion and outputting the patient description.

In one embodiment, the step of generating the patient description comprises accessing a database comprising a plurality of predefined patient descriptions each having associated thereto a respective lesion position and at least one respective property value and selecting the patient description amongst the plurality of predefined patient descriptions based on the desired position and the desired value.

In one embodiment, the method further comprises generating an electrocardiogram (ECG) graph and outputting the ECG graph.

In one embodiment, the step of generating the ECG graph comprises accessing a database comprising a plurality of predefined ECG graphs each having associated thereto a respective lesion position and at least one respective property value and selecting the ECG graph amongst the plurality of predefined ECG graphs based on the desired position and the desired value.

In one embodiment, the method further comprises receiving a desired value for at least one of an ST-segment elevation, a coronary artery disease and a calcification level.

According to another broad aspect, there is provided a system for training a healthcare professional to perform a percutaneous coronary intervention, the system comprising: a patient simulator configured for receiving a portion of an elongated instrument therein and applying a haptic feedback on the received portion of the elongated instrument; and a processing unit coupled to a memory, the processing unit being configured for: allowing a trainer to define a position of a lesion and at least one property of the lesion; and configuring the haptic feedback based on the position and properties of the lesion.

In one embodiment, the processing unit is configured for allowing the trainer to select the position of the lesion amongst a predefined number of possible lesion positions.

In one embodiment, the at least one property of the lesion comprises at least one of a length of the lesion, an occlusion percentage, a Thrombolysis In Myocardial Infarction (TIMI) flow grade and an eccentricity of the lesion.

In one embodiment, the processing unit is further configured for generating a patient description based on the defined position for the lesion and the at least one property of the lesion and providing the patient description for display.

In one embodiment, the step of generating the patient description comprises accessing a database comprising a plurality of predefined patient descriptions each having associated thereto a respective lesion position and at least one respective property value and selecting the patient description amongst the plurality of predefined patient descriptions based on the desired position and the desired value.

In one embodiment, the processing unit is further configured for generating an electrocardiogram (ECG) graph and providing the ECG graph for display.

In one embodiment, the step of generating the ECG graph comprises accessing a database comprising a plurality of predefined ECG graphs each having associated thereto a respective lesion position and at least one respective property value and selecting the ECG graph amongst the plurality of predefined ECG graphs based on the desired position and the desired value.

In one embodiment, the processing unit is further configured for receiving a desired value for at least one of an ST-segment elevation, a coronary artery disease and a calcification level.

According to a further embodiment, there is provided a computer-implemented method for training a healthcare professional to perform a percutaneous coronary intervention using an elongated instrument and a patient simulator, the computer-implemented method comprising: independently receiving: a selection of a position and a physical attribute for a first lesion; and a selection of a position and a physical attribute for a second lesion; processing a detected position and motion of the elongated instrument within the patient simulator and the selected position and physical attribute of each of the first and second lesion, to determine properties of a haptic feedback; and providing control signals causing the patient simulator to mechanically impart to the elongated instrument the haptic feedback having the determined properties.

In one embodiment, the physical attribute comprises at least one of a length of the lesion, an occlusion percentage, a Thrombolysis In Myocardial Infarction (TIMI) flow grade and an eccentricity of the lesion.

In one embodiment, the haptic feedback comprises at least one of a pulling force, a pushing force and a rotation.

According to still another broad aspect, there is provided a system for training a healthcare professional to perform a percutaneous coronary intervention using an elongated instrument and a patient simulator, the system comprising: a processor; and a non-transitory storage medium operatively connected to the processor, the non-transitory storage medium comprising computer-readable instructions; the processor, upon executing the computer-readable instructions, being configured for: independently receiving: a selection of a position and a physical attribute for a first lesion; and a selection of a position and a physical attribute for a second lesion; processing a detected position and motion of the elongated instrument within the patient simulator and the selected position and physical attribute of each of the first and second lesion, to determine properties of a haptic feedback; and providing control signals causing the patient simulator to mechanically impart to the elongated instrument the haptic feedback having the determined properties.

In one embodiment, the physical attribute comprises at least one of a length of the lesion, an occlusion percentage, a Thrombolysis In Myocardial Infarction (TIMI) flow grade and an eccentricity of the lesion.

In one embodiment, the haptic feedback comprises at least one of a pulling force, a pushing force and a rotation.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 11 schematically illustrates an exemplary healthy blood vessel;

FIG. 12 schematically illustrates the healthy blood vessel of FIG. 11 in which a fully collapsed concentric lesion has been created, in accordance with an embodiment;

FIG. 13 schematically illustrates the blood vessel of FIG. 12 in which the length of the fully collapsed concentric lesion has been adjusted to a desired length, in accordance with an embodiment;

FIG. 14 schematically illustrates the blood vessel of FIG. 13 in which the blockage percentage of the lesion has been adjusted to a desired value, in accordance with an embodiment;

DETAILED DESCRIPTION

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Figure 1:
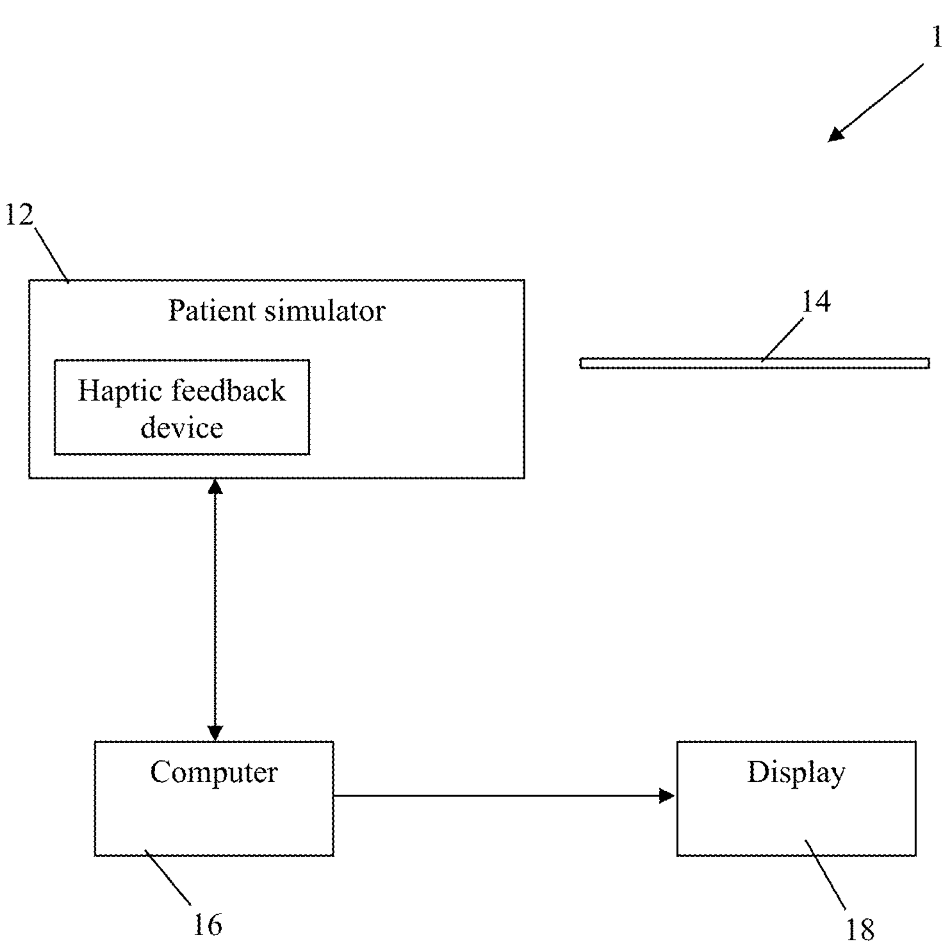
FIG. 1 is a block diagram illustrating a system for training a healthcare professional to perform percutaneous coronary interventions using elongated medical instruments, in accordance with an embodiment.

FIG. 1 illustrates one embodiment of a system 10 for training a user on medical procedure in which elongated medical instruments have to be introduced into a human body. More precisely, the system 10 is configured for training a user to perform a percutaneous coronary intervention, i.e., to treat a lesion present in a blood vessel such as a vein, an artery or any tubular anatomical structure. The illustrated system 10 comprises a patient simulator 12, an elongated medical instrument 14, a computer machine 16 and a display 18.

As known in the art, a patient simulator 12 comprises an opening or cavity in which the elongated medical instrument 14 is to be inserted by a user such as a healthcare professional. At least one sensor provided in the patient simulator 12 and/or mounted on the elongated instrument 14 measures the position and/or orientation of the elongated instrument 14 relative to the patient simulator 12. In one embodiment, the sensor is configured for measuring the position and/or orientation of the distal end of the elongated instrument 12 which is to be inserted into the patient simulator 12. In another embodiment, the sensor is configured for measuring the position and/or orientation of a point or portion of the elongated instrument 14 other than the distal end thereof, and the position and/or orientation of the distal end of the elongated instrument can be determined from the measured position and/or orientation.

The patient simulator 12 further comprises a haptic feedback device configured for providing a realistic haptic feedback on the elongated instrument 14 when inserted into the patient simulator 12. For example, the haptic feedback device may be configured for applying an insertion resistance force on the distal end of the elongated instrument 14 such as when the distal end of the elongated instrument 14 abuts against a lesion, applying a retraction resistance force on the distal end of the elongated instrument 14, applying a pushing force or a pulling force on the distal end of the elongated instrument 14 to simulate heart movement for example, and/or the like. Other examples of haptic feedbacks may comprise a pulsative feel of a heartbeat, a static feel when a balloon is inflated, increased resistance in the aorta or other vasculature, resistance while crossing tight lesions or tight vessels, resistance to a rotation of the elongated medical instrument 14, and/or the like.

The patient simulator 12 is in communication with the computer machine 16, e.g., the computer machine 16 is in communication with the sensor(s) and the haptic feedback device contained in the patient simulator 12. The computer machine 16 is provided with at least one processing unit, a memory or data storing unit and communication means. The computer machine 16 receives the measurement data from the sensor(s), i.e., the measured position and/or orientation of the distal end of the elongated instrument 14, and is configured to generate a simulated medical image based at least partially on the received measurement data. The simulated medical image comprises a representation of at least a portion of a body including the vessel in which the lesion is present and at least the distal end of the elongated instrument, the distal end of the elongated instrument being represented according to the measured position and/or orientation. In the present case, the simulated medical image comprises a representation of at least a portion of a heart and/or a blood vessel and at least the distal end of the elongated instrument 14.

The computer machine 16 is further in communication with the display 18 for displaying simulated medical images such as simulated X-ray images thereon to provide a visual feedback of the medical procedure to the user. It should be understood that the simulated medical images are displayed in substantially real-time so that the user may see the position and/or orientation of the distal end on the elongated instruments 14 on the display 18 while moving the elongated instrument 14 inserted into the patient simulator 12.

The computer machine 16 is further configured to control the haptic feedback device contained in the patient simulator 12. In one embodiment, the computer machine 16 is configured to generate a haptic feedback based on at least the position and/or orientation of the distal end of the elongated instrument 14 within the patient simulator 12 in substantially real-time. The computer machine 16 then transmits the determined haptic feedback to the haptic feedback device which executes the haptic feedback. As described above, a haptic feedback may be a retraction resistance force to be applied on a portion of the elongated instrument such as on the distal end of the elongated instrument 14, a pushing force or a pulling force to be applied on a portion of the elongated instrument 14 such as on the distal end of the elongated instrument 14 to simulate heart movement for example, and/or the like.

It should be understood that any adequate patient simulator 12 may be used. For example, the patient simulator 12 may be a manikin mimicking at least a portion of the body of a human being. In another example, the patient simulator 12 may be an elongated body provided with at least an opening or cavity for insertion of the elongated medical instrument 14 therein, a carriage for receiving therein the distal end of the elongated medical instrument 14, a rail along which the carriage is movable, and a motorized feedback device. It should be understood that the haptic feedback device may be any adequate motorized device connected to the carriage and adapted to apply a retraction resistance force, a pushing force or a pulling force and/or the like on the carriage and/or directly on the distal end of the elongated instrument 14.

It should be understood that the elongated medical instrument 14 may be any adequate elongated instrument that is usually used during medical procedures in which an elongated medical instrument has to be introduced into a body. For example, the elongated medical instrument may be a guidewire, a lead wire, a catheter, a delivery tube, a balloon or the like. In one embodiment, the elongated medical instrument 14 is a real medical instrument. In another embodiment, the elongated medical instrument 14 is a mock medical instrument.

The computer machine 16 further comprises a software component stored thereon that enables a trainer to create and customize training procedure cases. The software component allows the trainer to select a desired position for a lesion to be treated, i.e., to select a desired blood vessel and the location for the lesion on the selected blood vessel, and define some characteristics or properties of the lesion, as described below in greater detail. In one embodiment, the desired position for the lesion is selected amongst a list of predefined possible positions and values for the characteristics of the lesion can be inputted using a user interface.

Figure 2:
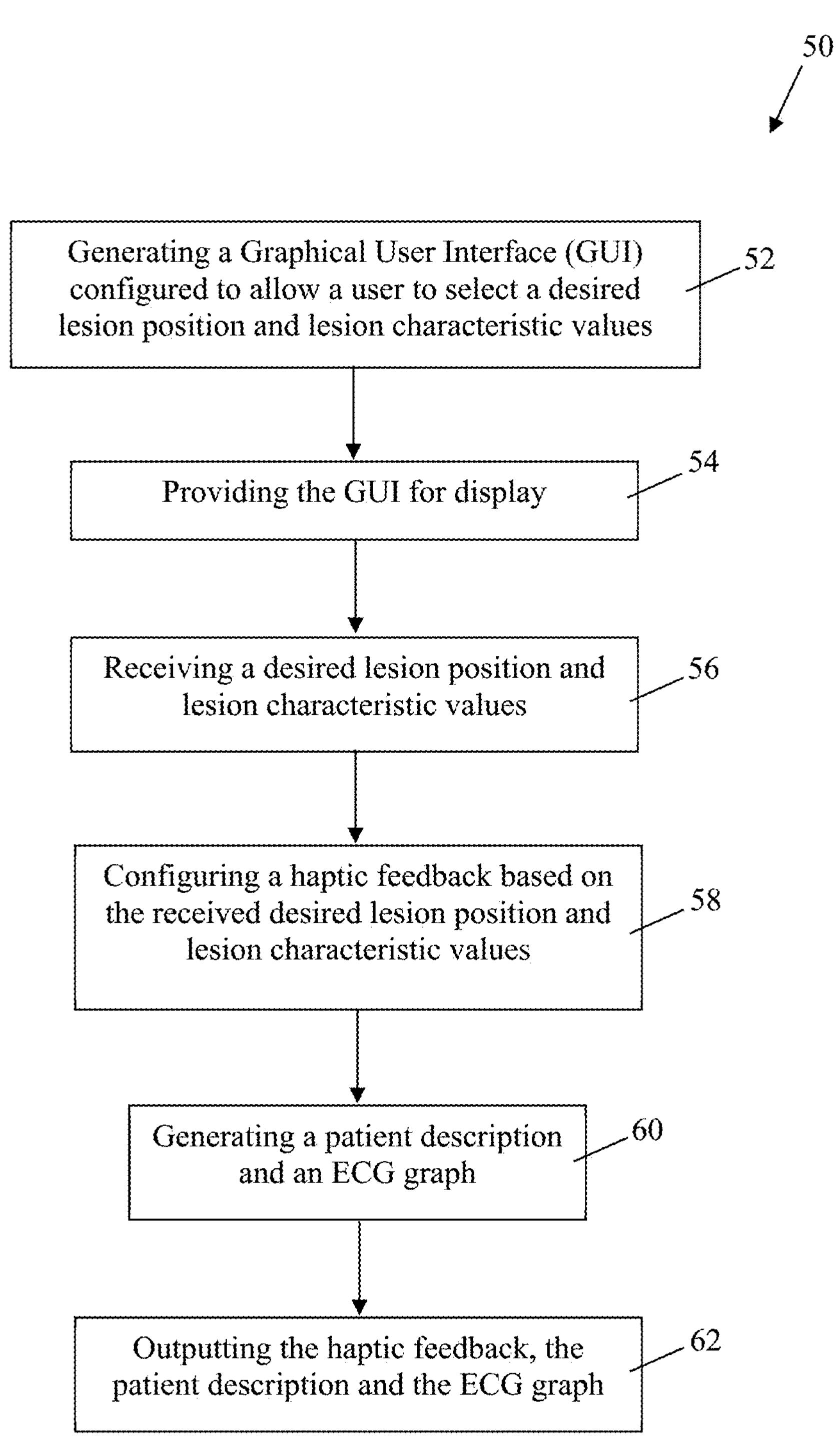
FIG. 2 is a flow chart illustrating a method for creating a customized training case, in accordance with an embodiment.

In the following there is described one exemplary computer-implemented method 50 that may be executed by the computer machine 16 for creating a customized training procedure scenario or case, as illustrated in FIG. 2.

At step 52, a Graphical User Interface (GUI) is generated. The GUI is an interactive GUI that allows the trainer to select a desired location for the lesion and the value of some characteristics for the lesion. The GUI comprises graphical control elements such as graphical widgets, scrollbars, sliders, input boxes, and/or the like for allowing the trainer to input values for the lesion characteristics.

In one embodiment, a list of predefined positions for the lesion is stored on the computer machine that executes the method 50 and the list of predefined positions is displayed in the GUI. Check boxes may each be associated with a respective predefined position for allowing the trainer to select a desired position. Text defining the respective position may be associated with each check box.

It should be understood that a position or location for a lesion is defined by an identification of a given blood vessel and a position of the lesion along the given blood vessel.

In another embodiment, an image of a heart and blood vessels may be contained in the GUI and the trainer may select the desired lesion position directly from the image of the heart and blood vessels. In one embodiment, the trainer may position a cursor at a desired position for a lesion and click on a button of a mouse or press a key of a keyboard, for example, to input the position of the cursor as the desired lesion position. In one embodiment, after the desired position for the lesion has been selected by the user, a visual indicator may be inserted in the image at the selected position to provide the user with a visual feedback of the selected position. In one embodiment, possible positions for lesions are predefined so that the trainer may select a desired lesion position amongst the predefined positions. In this case, a respective visual indicator may be inserted into the image at each possible position and the user may select a desired lesion position by a selecting the corresponding visual indicator such as by clicking on the visual indicator using a mouse.

In one embodiment, the characteristics/attributes for the lesion for which the trainer has to provide a value comprise the length of the lesion, the occlusion percentage, the Thrombolysis In Myocardial Infarction (TIMI) flow grade and/or the eccentricity of the lesion.

At step 54, the generated GUI is provided for display on a display such as display 18.

Using any adequate user interface such as a touch screen integrated into the display 18, a keyboard, a mouse and/or the like, the trainer selects the desired position for the lesion and inputs the values for the lesion characteristics. The selected position for the lesion and the lesion characteristics values are then transmitted by the user interface and received by the computer machine at step 56.

As described above, the desired position for the lesion may be selected by the trainer by checking a check box corresponding the desired position for the lesion when a list of predefined lesion positions each having a respective check box associated thereto are contained in the GUI. In another example in which the GUI comprises an image of a heart and blood vessels, the trainer may use a mouse to point at the desired position for the lesion and left-click to select the desired position for example.

At step 58, a haptic feedback is configured based at least on the received position for the lesion and the values for the lesion characteristics. In one embodiment, the haptic feedback is defined by a type of haptic feedback such as a pulling force, a pushing force, a rotation, or the like, and an amplitude for the haptic feedback such as a force amplitude.

In one embodiment and as better described below, the haptic feedback is determined based on a collision mesh.

At step 60, a patient description and an electrocardiogram (ECG) graph are generated based on the selected position for the lesion and the characteristics for the lesion inputted by the trainer.

In one embodiment, the patient description contains the age and sex of a patient. It also contains a description of the problem encountered by the patient, the symptoms experienced by the patient, any medical procedure already performed on the patient, a time of arrival to the hospital for the patient, a possible cause for a pathology and/or the like.

In one embodiment, the patient description is retrieved from a database stored on a memory such as on the memory of the computer machine 16 or on an external memory. The database comprises a plurality of different patient descriptions each associated with a respective lesion position and respective lesion characteristics values. In this case, the step of generating the patient description comprises retrieving from the database the given patient description that corresponds to the position for the lesion selected by the trainer and the lesion characteristic values inputted by the trainer. It should be understood that the selection of the given patient description can be performed based on the selected position for the lesion and only one or more lesion characteristic value, but not on all lesion characteristic values inputted by the trainer. For example, when the trainer is requested to input a value for four different lesion characteristics, the patient description may be generated based on the value inputted for only two predefined lesion characteristics in addition to the selected position for the lesion. In this case, the database may comprise a plurality of different patient descriptions each associated with a respective lesion position and only two respective lesion characteristics values.

In one embodiment, the ECG graph is retrieved from a database stored on a memory such as on the memory of the computer machine 16 or on an external memory. The database comprises a plurality of different ECG graphs each associated with a respective lesion position and respective lesion characteristics values. In this case, the step of generating the ECG graph comprises retrieving from the database the given ECG graph that corresponds to the position for the lesion selected by the trainer and the lesion characteristic values inputted by the trainer. Similarly to the selection of the given patient description, it should be understood that the selection of the given ECG graph can be performed based on the selected position for the lesion and only one or more lesion characteristic value, but not on all lesion characteristic values inputted by the trainer.

At step 62, the generated haptic feedback, patient description and ECG graph, and optionally the selected lesion position and the inputted lesion characteristic values are outputted. For example, they may be stored on a database of customized training procedure cases.

In one embodiment, a customized training procedure case comprises a selected position for the lesion, selected lesion characteristics values and the haptic feedback generated based on the selected position for the lesion and the selected lesion characteristics values. However, it should be understood that a customized training procedure case may also comprise additional information such as the patient description and/or the ECG graph generated based on the selected position for the lesion and the selected lesion characteristics values.

While the method 50 is described above with respect to the selection of a single lesion, it should be understood that the method 50 may be adapted to allow a trainer to create two or more lesions for a same customized training procedure case. In this case, the trainer selects at least two different lesion positions and inputs lesion characteristic values for each lesion position, thereby defining two lesions.

In one embodiment, the trainer independently selects/inputs the position and at least one physical attribute value for a first lesion, and the position and at least one physical attribute value for a second lesion. In this case, the computer machine 16 independently receives the position and the physical attribute for the first and second lesions. During the simulation, the computer machine 16 is configured for processing the detected position and the motion of the elongated instrument 14 within the patient simulator 16 and the selected position and physical attribute for the first and second lesions to determine properties of the haptic feedback. The computer machine 16 is further configured for providing control signals causing the patient simulator 12 to mechanically impart to the elongated instrument the haptic feedback having the determined properties.

It should also be understood that the step 60 may be omitted. In this case, the step 62 comprises outputting the haptic feedback and optionally the selected lesion position and the inputted lesion characteristic values.

Figure 3:
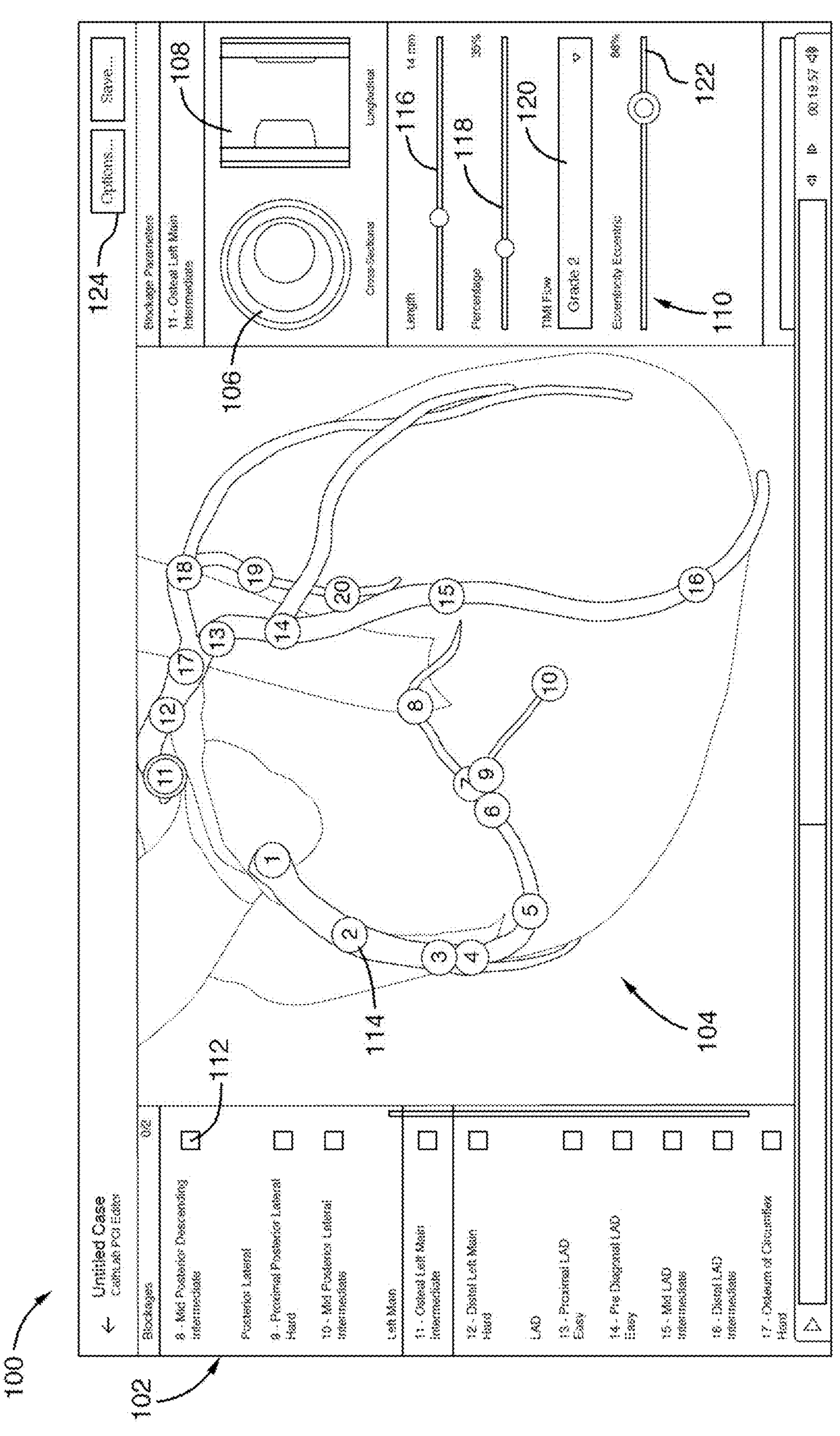
FIG. 3 is a first exemplary Graphical User Interface (GUI) to be presented to a trainer for the creation of a customized training case.

FIG. 3 illustrates an exemplary GUI 100 that may be displayed to the trainer at step 54 of the method 50. The GUI 100 comprises a list 102 of predetermined possible positions for a lesion, an image 104 of a heart and surrounding blood vessels, a first cross-sectional image 106 of a blood vessel, a second-cross-sectional image 108 of the blood vessel 108, and a section 110 for inputting lesion characteristic values.

As illustrated, a check box 112 and a written lesion position description is associated with each possible lesion position for allowing a trainer to select a desired lesion position and a scrollbar is provided for allowing the trainer to navigate through the list 102 of possible positions. Furthermore, a respective number and a respective difficulty level is associated with each possible lesion position.

The image 104 of the heart and surrounding blood vessels is provided with visual indicators in the shape of icons 114. Each icon 114 is associated with a respective possible lesion position of the list 102 and is provided with the same number as the one provided to its respective lesion position of the list 102. Furthermore, each icon 114 is positioned at its respective possible lesion position on one of the blood vessels illustrated in the image 104.

The image 106 is a schematic representation of the cross-section of the blood vessel at the lesion taken along a transverse plane, i.e., along a plane orthogonal to the longitudinal axis of the blood vessel, and represents a transverse cross-sectional view of the lesion and the blood vessel. From the image 106, one can see the shape, position and size of the lesion within the transverse plane, and particularly the eccentricity and the blockage percentage of the lesion.

The image 108 is a schematic representation of the cross-section of the blood vessel at the lesion taken along a longitudinal plane, i.e., along a plane parallel to the longitudinal axis of the blood vessel, and represents a longitudinal cross-sectional view of the lesion and the blood vessel. From the image 108, one can see the shape, position and size of the lesion within the longitudinal plane, and particularly the length and the blockage percentage of the lesion.

The section 110 is configured for allowing the trainer to input desired values for the length of the lesion, the blockage percentage and the eccentricity of the lesion and also the value for the TIMI flow grade. The TIMI flow grade allows the system to provide different speeds of flow when the user performs contrast injections. Slower speeds (i.e., lower values for the TIMI flow grade) are visual indicators to the learner that the lesion needs to be treated. The section 110 comprises a first slider 116 for inputting a value for the length of the lesion, a second slider 118 for inputting a value for the blockage percentage associated with the lesion (i.e., the percentage of the transverse cross-section of the blood vessel that is blocked by the lesion), a dropdown list 120 for inputting a desired value for the TIMI flow grade and a third slider 122 for inputting a desired value for the eccentricity of the lesion.

It should be understood that the images 106 and 109 are interactive, i.e., they are modified according to the values inputted in the section 110. If the trainer modifies the value of a lesion characteristic, new images 106 and 108 are generated based on the newly inputted value for the lesion characteristic and inserted into the GUI 100 at heir respective position to obtain an updated GUI 100 which is then provided for display.

It should be understood that the method 100 further comprises a step of generating the image 104 of the heart and surrounding blood vessels and a step of inserting the image 104 into the GUI 100 before the step 54 of providing the GUI for display. In one embodiment, the image 104 is generic and does not depend on the lesion characteristic values inputted by the trainer. In one embodiment, the step of generating the image 104 comprises retrieving the image 104 from a database.

It should also be understood that the method 100 further comprises a step of generating the images 106 and 108 according to the received values for the length, blockage percentage and eccentricity for the lesion, a step of updating the GUI by inserting the generated images 106 and 108 into the GUI 100 and a step of providing the updated GUI 100 for display. In one embodiment, no images 106 and 108 are displayed to the trainer until a selection of a desired lesion position and an input of desired lesion characteristic values. In another embodiment, images 104 and 106 illustrating the blood vessel only are displayed to the trainer before any selection of a desired lesion position and any input of desired lesion characteristic values. Once a desired lesion position has been selected and desired lesion characteristic values are inputted, the images 106 and 108 are updated to illustrate the lesion within the blood vessel according to the inputted lesion characteristic values to provide the trainer with a visual indication of the designed lesion.

In one embodiment, the blood vessel represented in the images 106 and 108 is generic, i.e. the same transverse and longitudinal cross-sectional views of a blood vessel are generated independently of the selected position for the lesion and the inputted lesion characteristics values. In this case, only the representation of the lesion in the images 106 and 108 is modified according the inputted values for the lesion characteristics.

While in the illustrated embodiment, the list 102 is located on the left of the GUI 100, the image 104 is located at the center of the GUI 100, the images 106 and 108 are position side-by-side at the top right of the GUI 100 and the characteristic input section 110 is located on the right of the GUI 100 below the images 106 and 108, it should be understood that other arrangement of the list 102, the images 104, 106 and 108 and the section 110 are possible.

It should be understood that the GUI 100 is exemplary only and any adequate interactive graphical control element or widgets that allow the trainer to select a desired lesion position and input desired values for the lesion characteristics may be used. For example, instead of displaying the list 102 and the check boxes 112, a dropdown list can be used for presenting the possible lesion positions to the trainer. In another example, the sliders 116, 118 and 122 may be replaced with text boxes in which the trainer may enter desired values.

In one embodiment, the images 106 and 108 are part of the customized training procedure case created by the trainer and stored in the database of cases.

Figure 4:
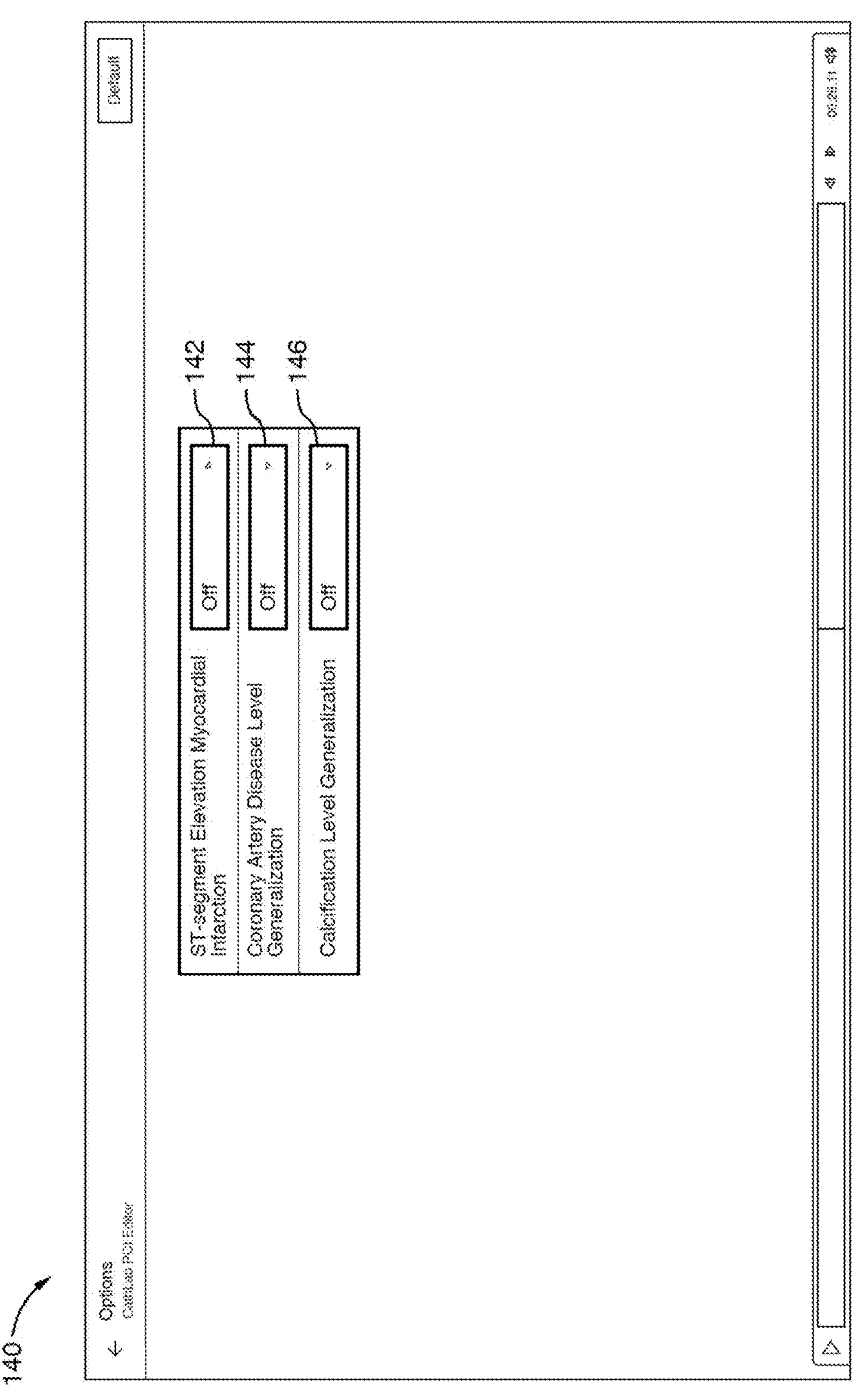
FIG. 4 is a second exemplary GUI to be presented to a trainer for the creation of a customized training case.

In one embodiment, the GUI 100 further comprises a button 124 for allowing the trainer to access options. Upon activation of the button 124 by the trainer, an indication of the activation of the button 124 is received and a further GUI such as the GUI 140 illustrated in FIG. 4 is generated and provided for display. The illustrated GUI 140 allows the user to select a desired value for the three following parameters: ST-segment elevation, coronary artery disease and calcification level. The ST-segment elevation parameter indicates an ST segment Elevation Myocardial Infarction (STEMI) which is an emergent procedure that has associated changes on the ECG and is what is commonly known as a heart attack. This ST-segment elevation parameter is selectable as on or off. The coronary artery disease parameter refers to a condition that causes generalized degradation of all coronary arteries, making the vasculature look ratty under contrast injection. The coronary artery disease parameter may be set to off, mild, moderate, or severe. The calcification level parameter refers to the amount of hardened calcium deposits that are visually demonstrated around the vessel. The calcification level parameter may be set to off, mild, moderate, or severe. In the illustrated embodiment, the values for the ST-segment elevation, coronary artery disease and calcification level can be selected using the dropdown lists 142, 144 and 146. It should be understood that the GUI 140 may contain other means for inputting values for the ST-segment elevation, coronary artery disease and calcification level. For example, the dropdown lists 142, 144 and 146 could be replaced with text boxes.

In order to train for treating a lesion present on a blood vessel, a user such as a healthcare professional accesses a given training procedure case of the database of different cases using the computer 16. In one embodiment, an indication of the given training procedure case to be performed may be transmitted to the user by a trainer. In another embodiment, the user may select the given training procedure case from a list of training procedure cases. In another embodiment, the given training procedure case may be randomly selected by the computer machine 16.

In one embodiment, a difficulty level is associated with each training procedure cases stored in the database. For example, three difficulty levels may exist, e.g. easy, intermediate and hard. In this case, the user may be requested to choose a desired difficulty level and the computer machine 16 may be configured for randomly selecting a given training procedure case having the desired difficulty level from the database of cases.

Once the user opens the given training procedure case, the computer machine 16 retrieves the patient description and the ECG graph, if any, corresponding to the given training procedure case and provides the retrieved patient description and ECG graph for display on the display 18. From the patient description and the ECG graph the user may estimate the type of lesion experienced by the patient and/or the location of the lesion and optionally decide whether a femoral or a right radial procedure should be performed.

Figure 5:
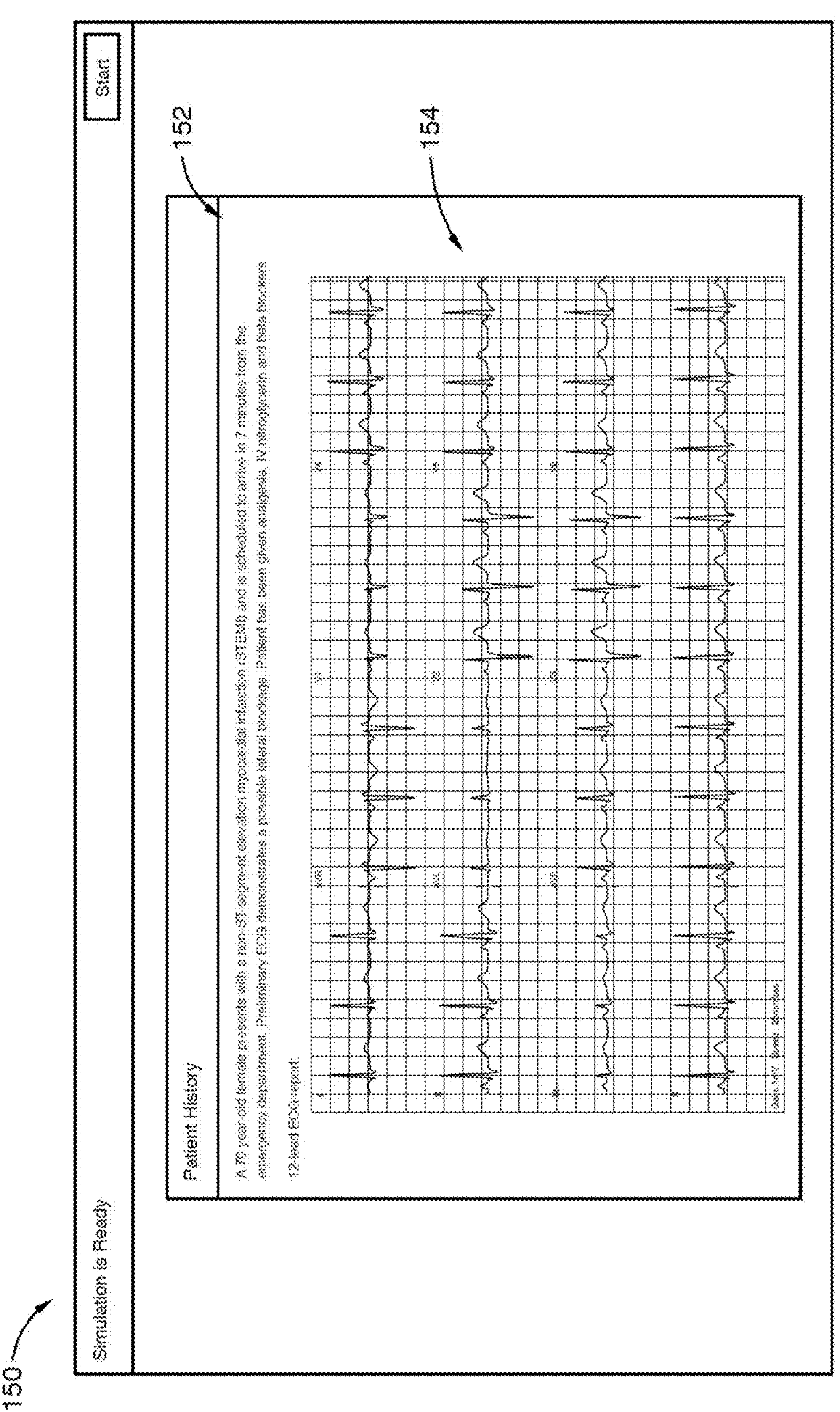
FIG. 5 is an exemplary GUI comprising a patient description and an Electrocardiogram (ECG) graph.
Figure 6:
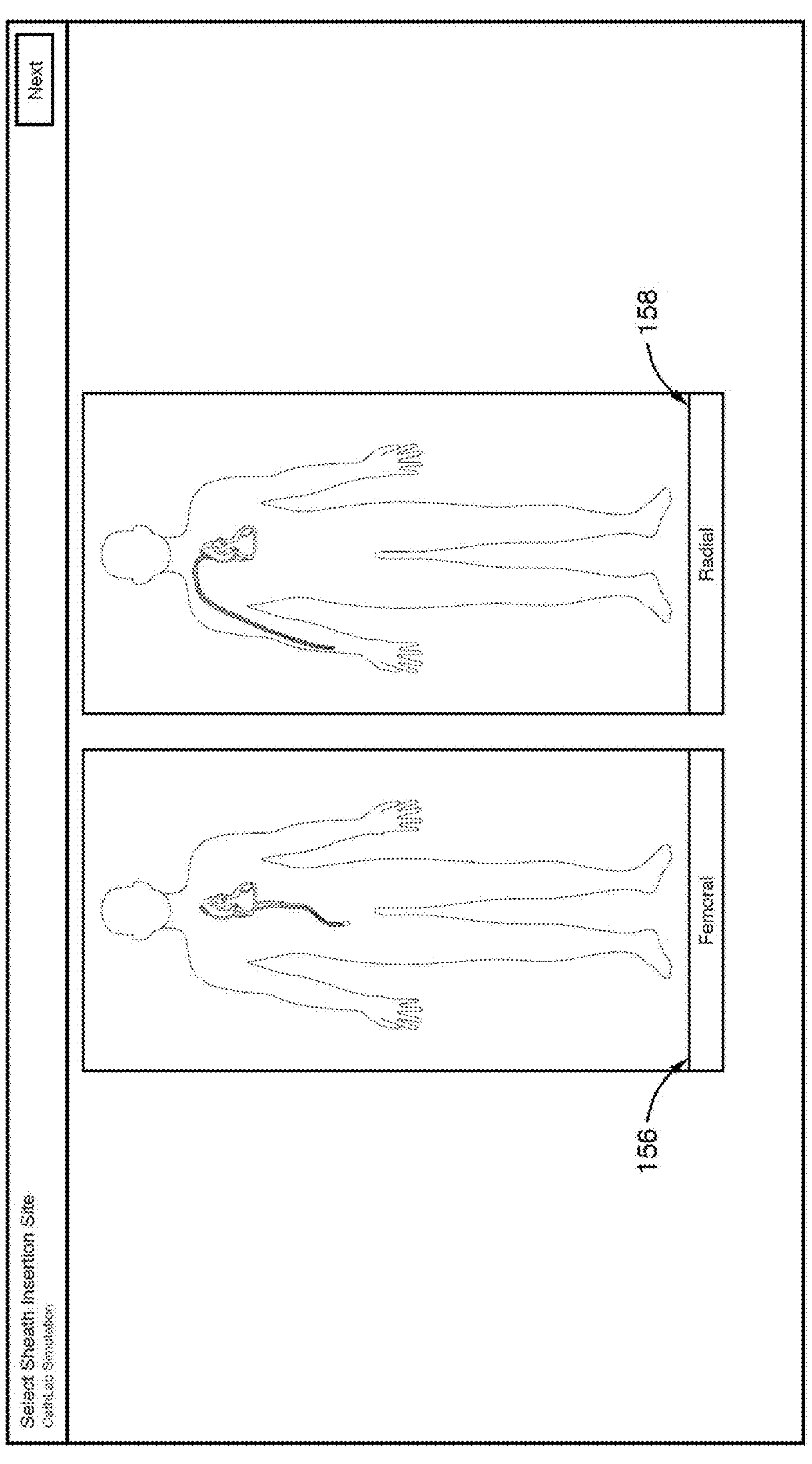
FIG. 6 is an exemplary GUI allowing a user to select between a femoral procedure mode and a radial procedure mode.

FIG. 5 illustrates an exemplary GUI 150 generated by the computer machine 16 for presenting the patient description and the ECG graph to the user. The GUI 150 comprises the patient description 152 and an ECG graph 154. FIG. 6 illustrates an exemplary GUI 155 comprising two buttons 156 and 158 each associated with a respective procedure mode for allowing the user to select a desired procedure mode. The button 156 is indicative of the femoral procedure and the button 158 is indicative of the radial procedure.

Figure 7:
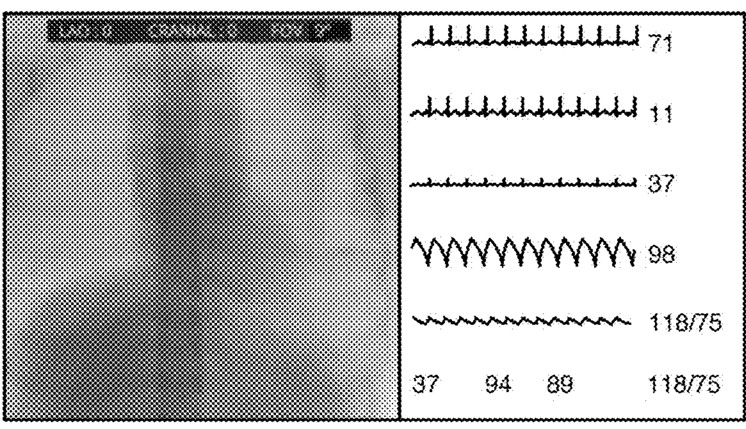
FIG. 7 is an exemplary image to be displayed to a healthcare professional during training, the exemplary image comprising a simulated image of a portion of a body and an ECG graph.

The computer machine 16 receives the selection for the procedure mode and starts the training simulation. A simulated medical image representing a part of a body such a heart is displayed on the display 18. FIG. 7 illustrates an exemplary medical image that can be displayed on the display 18 during the training of the user. The exemplary medical image comprises a simulated medical image of a portion of a body, an ECG graph and other medical or vital sign data.

The user is instructed to insert an elongated medical instrument 14 in the patient simulator 12. As the user inserts the elongated medical instrument 14 within the patient simulator 12, the computer machine 16 updates the displayed medical image so that it comprises a representation of at least the distal section of the elongated medical instrument 14. The computer machine 16 receives from the patient simulator 12 the position of the distal end of the elongated medical instrument 14 within the patient simulator 12 and compares the received position to the lesion position contained in the given training procedure case. When the received position of the elongated medical instrument 14 within the patient simulator 12 corresponds to the lesion position, the computer machine 16 triggers the haptic feedback device to execute the haptic feedback effect contained in the given training procedure case. This provides the user with a realistic feedback feeling.

In one embodiment, an animated anatomy is displayed to the user during the training. The animated anatomy comprises at least one blood vessel in which the lesion to be treated is present. The animated anatomy is generated based on a configurable 3D anatomy which is customized using the inputs received from the trainer, i.e., the position, length, eccentricity and blockage percentage of the lesion.

Figure 8:
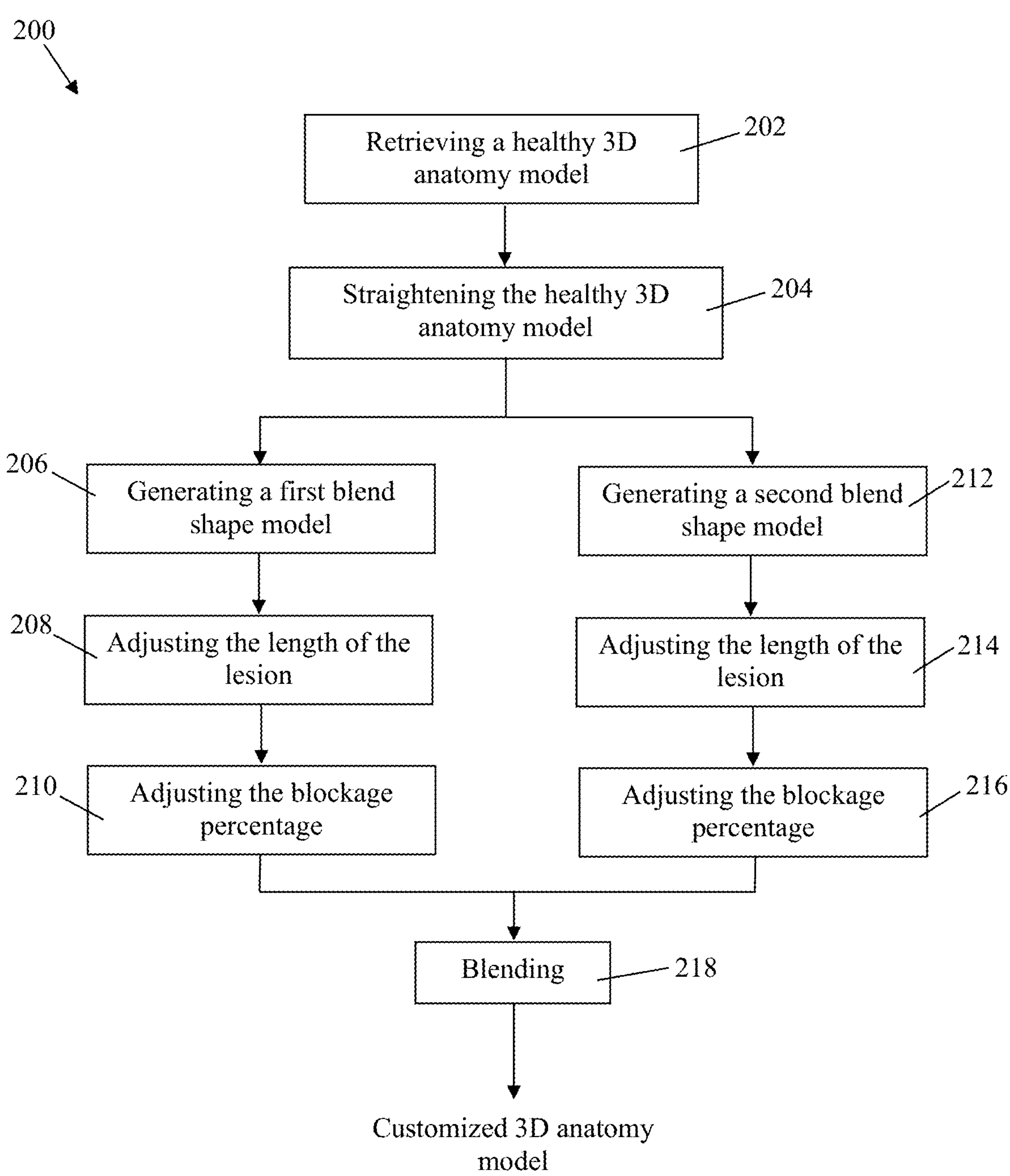
FIG. 8 is a flow chart illustrating a method for customizing a healthy 3D anatomy model using lesion characteristics imputed by a trainer.

FIG. 8 illustrates an exemplary computer-implemented method 200 for generating a 3D anatomy model using the lesions characteristics inputted by the trainer.

At step 202, a healthy 3D anatomy model comprising at least the blood vessel in which the lesion is to be simulated is retrieved. The healthy 3D anatomy model is a 3D simulation of the anatomy that is configurable/customizable using the lesion characteristic values inputted by the trainer. It should be understood that the blood vessel(s) comprised in the healthy 3D anatomy model contain(s) no lesion.

In one embodiment, the heathy 3D anatomy model is an animation of a 3D anatomy comprising at least one blood vessel. The animation is a collection of vertices, edges and polygons that form the surface of 3D anatomy model. In one embodiment, the polygons comprises either quadrangles or triangles.

Figure 9:
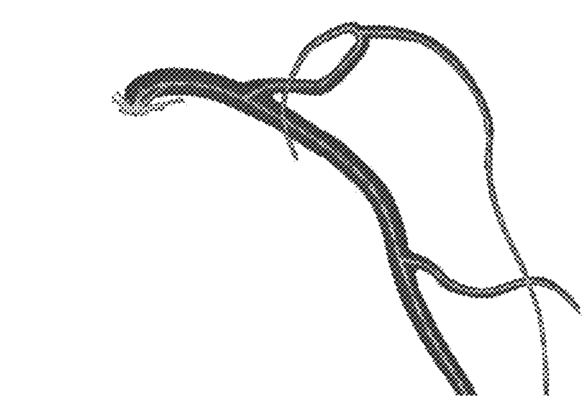
FIG. 9 illustrates exemplary blood vessels of a healthy 3D anatomy model.

FIG. 9 illustrates an exemplary healthy 3D anatomy model. In this model, the two coronary arteries are modeled using a weighted tree representing its central line and its local radius. In one embodiment, only the first two levels of intersections are represented.

At step 204, the coronary trees are then straightened, thereby obtaining a straightened healthy 3D anatomy model. The straightening step limits the artifacts in the blend shapes animations. When dealing with non-trivial shapes, blend shapes may lead to strange intermediary results with surfaces locally collapsing for instance. Straightening the geometry allows for reducing this risk.

Figure 10:
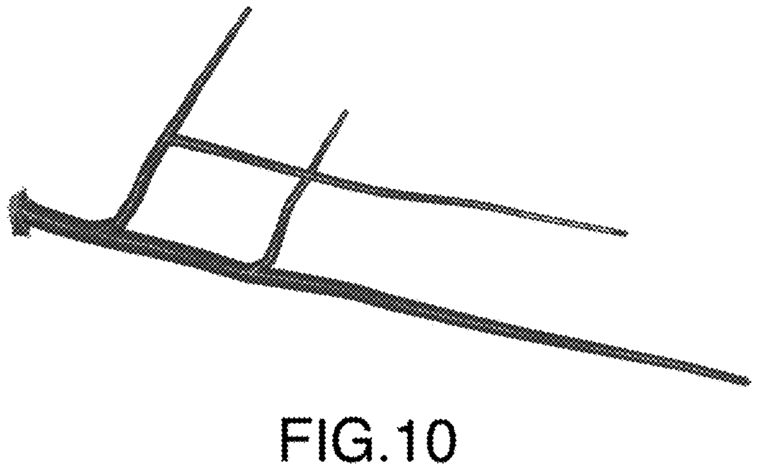
FIG. 10 illustrates the blood vessels of FIG. 9 after being straightened.

FIG. 10 illustrates the straightened healthy 3D anatomy model obtained from the healthy 3D anatomy model of FIG. 9.

At step 206, a first blend shape model is generated from the straightened healthy 3D anatomy model. The first blend shape model corresponds to the straightened healthy 3D anatomy model in which a fully collapsed concentric lesion has been added in the blood vessel selected by the trainer at the location selected by the trainer. In one embodiment, the length of the fully collapsed concentric lesion generated at step 206 corresponds to a minimal length such as the size of a mesh unit. For example, the minimal length for the lesion may be 4 mm.

FIG. 11 schematically illustrates a healthy blood vessel in which a lesion is to be added. The healthy blood vessel corresponds to the blood vessel selected by the trainer and in which a lesion is to be added. FIG. 12 illustrates the healthy blood vessel of FIG. 10 in which a fully collapsed concentric lesion has been added at the position selected by the trainer.

At step 208, the first blend shape model is modified so that the lesion inserted therein be provided with the lesion length selected by the trainer, i.e., the length of the lesion generated at step 206 is adjusted to the length selected by the trainer.

FIG. 13 schematically illustrates the blood vessel of FIG. 12 in which the length of the lesion has been adjusted to correspond to the lesion length selected by the trainer.

In one embodiment, the lesion position selected by the trainer corresponds to the position of one end of the lesion. In another embodiment, the lesion corresponds selected by the trainer corresponds to a reference point other than the extremities such as the middle or center of the lesion.

In an embodiment in which the lesion position selected by the trainer corresponds to the position of one end of the lesion, the lesion is extended into one of two possible directions at 208. The two possible directions are the upstream direction or the downstream position. It should be understood that the given direction in which the lesion is extended so as to provide the lesion with the desired length is predefined. In the embodiment illustrated in FIGS. 12 and 13, the lesion is extended in the downstream direction, i.e., towards the right side of the blood vessel.

In an embodiment in which the lesion position selected by the trainer corresponds to the center of the lesion, the lesion is extended evenly on both sides of the lesion position so as to provide the lesion with the length selected by the trainer.

In an embodiment in which a minimal length for the lesion exists, all possible values for the length of a lesion is a multiple of the minimal length. For example, possible lengths for the lesion may include the minimal length, twice the minimal length, three times the minimal length, four times the minimal length, etc.

At step 210, the first blend shape model is further modified so that the blockage percentage of the lesion corresponds to the blockage percentage selected by the trainer.

FIG. 14 schematically illustrates the blood vessel of FIG. 13 for which the blockage percentage of the lesion has been modified to correspond to the blockage percentage selected by the trainer. In the illustrated embodiment, the blockage percentage is 30%.

The output of step 210 corresponds to the first blend shape model in which the length and the blockage percentage of the lesion correspond to the values selected by the trainer.

At step 212, a second blend shape model is generated from the straightened healthy 3D anatomy model. The second blend shape model corresponds to the straightened healthy 3D anatomy model in which a fully collapsed eccentric lesion has been added in the blood vessel selected by the trainer at the location selected by the trainer. In one embodiment, the length of the fully collapsed eccentric lesion generated at step 212 corresponds to the same minimal length as for the fully collapsed concentric lesion.

Figures 15, 16, 17, 18:
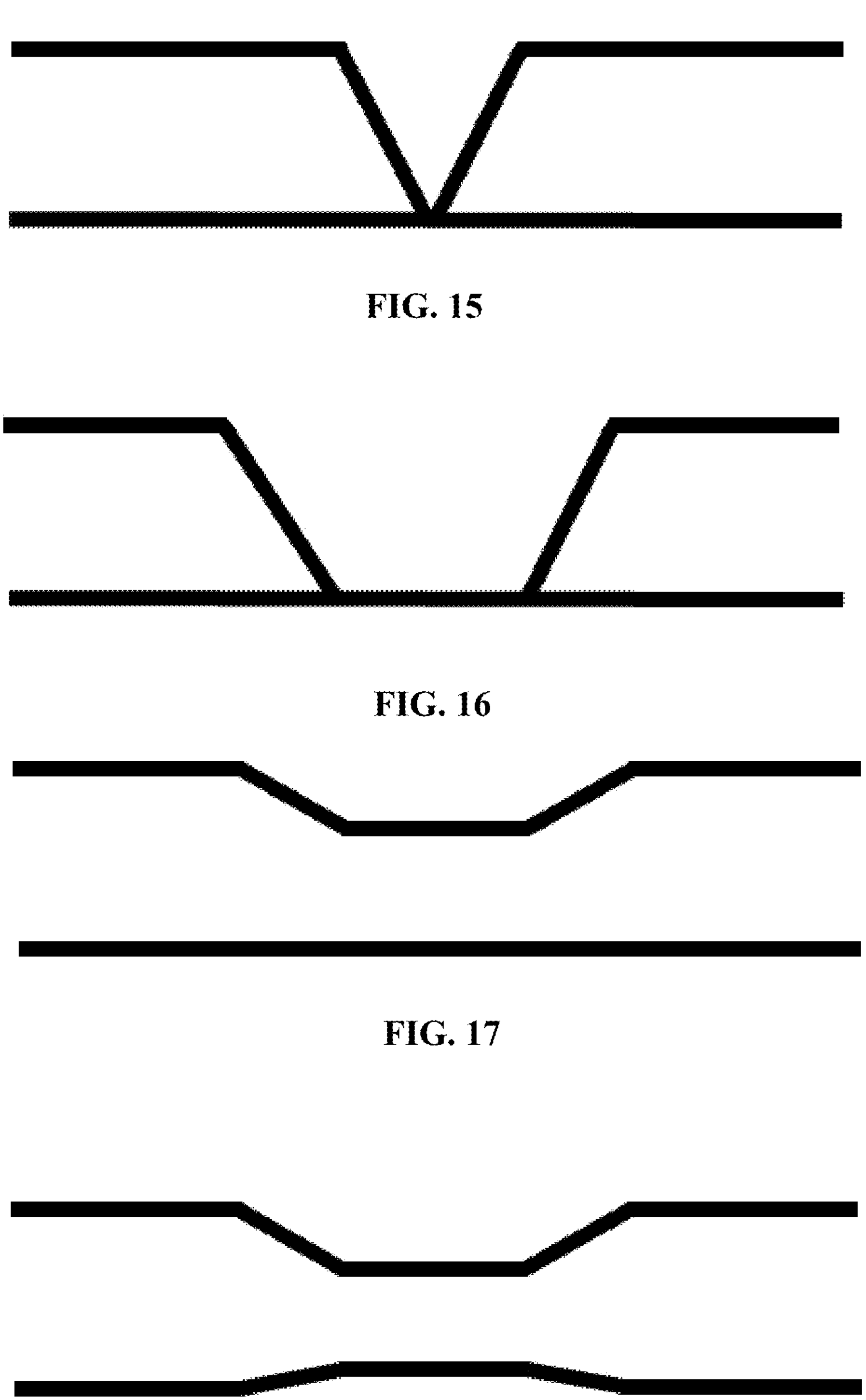
FIG. 15 schematically illustrates the healthy blood vessel of FIG. 11 in which a fully collapsed eccentric lesion has been created, in accordance with an embodiment.
FIG. 16 schematically illustrates the blood vessel of FIG. 15 in which the length of the fully collapsed eccentric lesion has been adjusted to a desired length, in accordance with an embodiment.
FIG. 17 schematically illustrates the blood vessel of FIG. 16 in which the blockage percentage of the lesion has been adjusted to a desired value, in accordance with an embodiment.
FIG. 18 schematically illustrates the blood vessel resulting from the blending of the blood vessel of FIG. 14 and the blood vessel of FIG. 17, in accordance with an embodiment.

FIG. 15 illustrates the healthy blood vessel of FIG. 10 in which a fully collapsed eccentric lesion has been added at the position selected by the trainer. It should be understood that the position of the fully collapsed eccentric lesion illustrated in FIG. 15 is the same position as that of the fully collapsed concentric lesion illustrated in FIG. 11.

At step 214, the second blend shape model is modified so that the lesion inserted therein be provided with the lesion length selected by the trainer, i.e., the length of the lesion generated at step 212 is adjusted to the length selected by the trainer. It should be understood that the lesion of the fully collapsed eccentric lesion is the same as that of the fully collapsed concentric lesion illustrated in FIG. 13.

FIG. 16 schematically illustrates the blood vessel of FIG. 14 in which the length of the lesion has been adjusted to correspond to the lesion length selected by the trainer.

It should be understood that the extension of the fully collapsed eccentric lesion is performed in a manner similar to that of the fully collapsed concentric lesion.

In an embodiment in which the lesion position selected by the trainer corresponds to the position of one end of the lesion, the fully collapsed eccentric lesion is extended along the same direction as that for the fully collapsed concentric lesion. In the embodiment illustrated in FIGS. 15 and 16, the lesion is extended in the downstream direction, i.e., towards the right side of the blood vessel.

In an embodiment in which the lesion position selected by the trainer corresponds to the center of the lesion, the lesion is extended evenly on both sides of the lesion position so as to provide the lesion with the length selected by the trainer.

In an embodiment in which a minimal length for the lesion exists, all possible values for the length of a lesion is a multiple of the minimal length. For example, possible lengths for the lesion may include the minimal length, twice the minimal length, three times the minimal length, four times the minimal length, etc.

At step 216, the second blend shape model is further modified so that the blockage percentage of the lesion corresponds to the blockage percentage selected by the trainer.

FIG. 17 schematically illustrates the blood vessel of FIG. 13 for which the blockage percentage of the lesion has been modified to correspond to the blockage percentage selected by the trainer. It should be understood that the blockage percentage applied to the lesion of FIG. 16 is equal to that applied to the corresponding concentric lesion, i.e., the lesion of FIG. 13. In the illustrated embodiment, the blockage percentage is 30%.

The output of step 216 corresponds to the second blend shape model in which the length and the blockage percentage of the lesion correspond to the values selected by the trainer.

It should be understood that the positions of the extremities of the lesion generated in the modified first blend shape model along the blood vessel selected by the trainer and the positions of the extremities of the lesion generated in the modified second blend shape model along the blood vessel selected by the trainer are identical. Similarly, it should be understood that the blockage percentage of the lesion generated in the first blend shape model and the blockage percentage of the lesion generated in the second blend model selected by the trainer are identical.

At step 218, the modified first and second blend shape models obtained at steps 210 and 216, respectively, are blended together based on the eccentricity value inputted by the trainer to obtain a customized 3D anatomy model that corresponds to the inputs received from the trainer. The customized 3D anatomy model is then outputted and stored in memory.

FIG. 18 illustrates the lesion obtained when the first and second modified blend shape models illustrated in FIGS. 14 and 17 are blended using an eccentricity of 50%.

In one embodiment, steps 206-210 and steps 212-216 are performed in parallel. In another embodiment, steps 206-210 are performed prior to performing steps 212-216. In a further embodiment, steps 212-216 are performed prior to performing steps 206-210.

In one embodiment, step 204 is omitted. In this case, steps 206-210 and steps 212-216 are performed directly using the un-straightened heathy 3D anatomy model.

In one embodiment, additional blend shapes may have been added to set the direction of the eccentricity and/or to give an ellipsoidal shape to the lesion rather than a spherical shape for example.

In one embodiment, the customized 3D anatomy model is outputted as an Fbx file or in any other format that supports blend shape animation.

The customized 3D anatomy model is used by a simulation engine for displaying images of the lesion created by the trainer and training a user such a medical practitioner. During the training, the user inserts an elongated instrument into the patient simulator 12 and the simulation engine inserts a representation of at least the distal end of the elongated medical instrument in the displayed images to provide a visual feedback of the position of the elongated instrument relative to the lesion. As described above, the patient simulator 12 is provided with a haptic feedback device for providing a haptic feedback on the elongated medical instrument inserted into the patient simulator 12.

The simulation engine is further configured for determining the type and the amplitude for the haptic feedback based on interactions between the collision mesh, the simulated elongated instrument and the anatomy contained in the customized 3D anatomy model (e.g., the lesion).

It should be understood that different characteristics for a lesion will impact the collision mesh formed between the simulated medical instrument and the simulated lesion which will result in different haptic feedbacks such as different types and/or amplitudes for the haptic feedback.

In one embodiment, the simulation engine is an agnostic data driven software that provides all the generic algorithms used in the simulation. The simulation engine may be seen as being similar to a game engine, but with a more advanced support of real-time deformable models. The geometrical description of the scene may be provided through a set of xml files and 3D assets generated by common 3D content creation software (e.g., Maya, Blender or the like) and the logic of the simulation may be provided though a set of Lua files.

The configuration provided by the trainer may be stored in form of a j son file, which may be loaded by the simulation engine and the different lesion animations may be adjusted to the corresponding parameter, which defines the geometry of blood vessels with the selected lesion.

The simulation may then be run using the geometry defined above as input data and the haptic feedback is determined using the following collision mesh method. The elongated instrument used during the training may be modelled using a 1D finite element model such as a 1D finite element model based on Cosserat Rods model and may interact with the geometrical mesh of the blood vessels obtained using the method 200 using a penalty method such as a penalty contact scheme. In one embodiment, the geometry of the blood vessels is not deformable and only the part of the blood vessel that corresponds to the lesion is given a specific elasticity that allows the penetration of the simulated elongated instrument. This part of the blood vessel may be distinguished from the others using the fact that, due to the animations, the position of the part of the blood vessel in time differs from its original position.

While the modeled elongated instrument interacts with the 3D representation of the geometrical mesh of the blood vessels, the contacts between the elongated instrument and the vessels are detected and generate penalty forces that are applied back to the elongated instrument model in order to maintain its position in the lumen of the vessel in which it is inserted. The penalty forces applied to the Cosserat rod model generate in all point of the model a stretch value which may be positive or negative. The haptic feedback is then obtained from the stretching of the elongated instrument model. The haptic force transmitted to the user is directly proportional to the stretching of the elongated instrument model, computed in the elongated instrument insertion point. If the stretch value is positive, the haptic feedback force prevents the user from retracting the elongated instrument. Alternatively, if the stretch value is negative, the haptic feedback force prevent the user from further inserting the elongated instrument.

While in the above description the haptic feedback is determined using a collision mesh method, it should be understood that any adequate method for determining a haptic feedback may be used.

In at least some embodiments, the haptic feedback is computed by using characteristics from the haptic feedback device, which allows the user to naturally feel the resistance due to the lesion.

For example, if the hole in the lesion is smaller, the resistance felt by the user while pushing the elongated instrument though the lesion will be greater. If the hole in the lesion is at a different location, then the location at which haptic resistance is felt by the user will be different. If the lesion is shorter, then the drop of haptic resistance felt after crossing the lesion will felt sooner, etc.

While the above description refers to a single computer machine 16 for both creating the training procedure case and executing the training simulation, it should be understood that at least two different computer machines may be used. For example, a first computer machine may be used for creating training procedure cases and a second computer machine may be used for controlling the patient simulator 12 and generating images to be displayed on the display 18 during the training of the user.

It should be understood that any adequate display 18 may be used for the training of a user. In one embodiment, the display 18 is a monitor connected to the computer machine 16. In another embodiment, the computer machine 16 is a laptop and the display 18 is the screen of the laptop. In a further embodiment, the display 18 comprises a virtual reality display, such as virtual reality glasses or a virtual reality headset, on which a virtual display, a virtual representation of a medical imaging apparatus such as a C-arm X-ray apparatus and additional information may be displayed. It should be understood that in this case the computer machine 16 is configured for generating the virtual display, the virtual representation of a medical imaging apparatus and the additional information and transmitting the generated elements to the virtual reality display for being displayed thereon.

Figure 19:
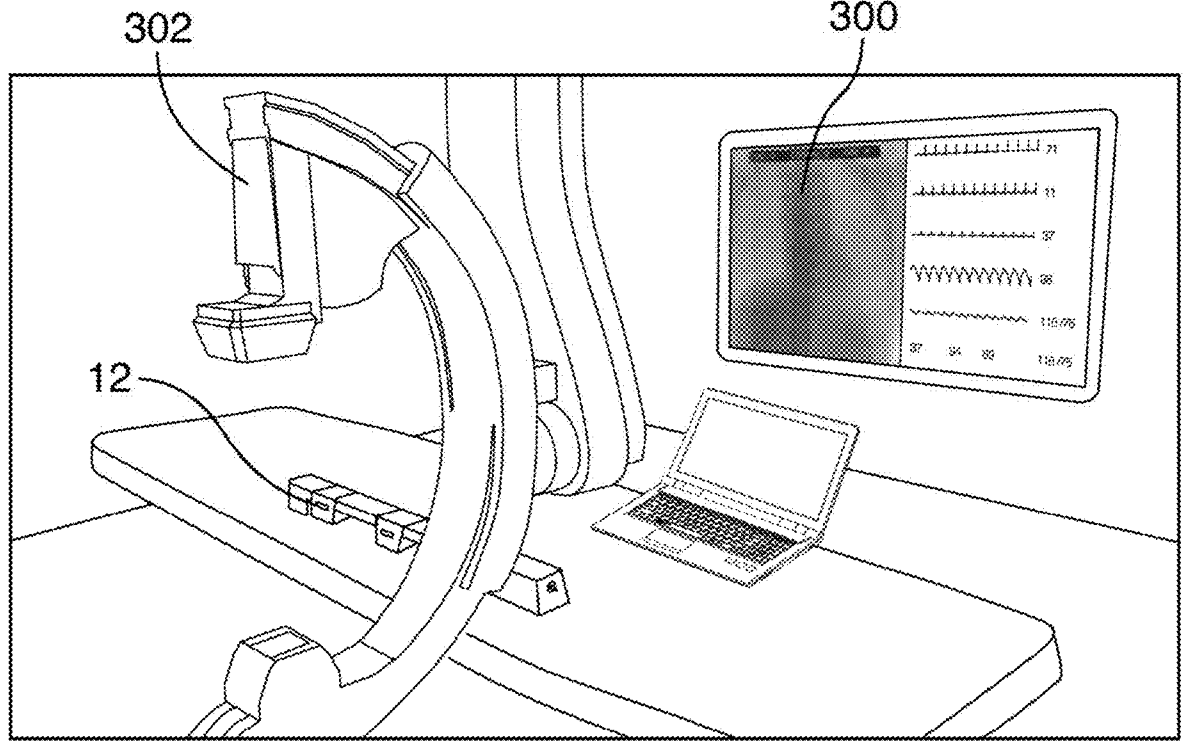
FIG. 19 illustrates an exemplary virtual reality view as experienced by a user wearing a virtual reality display.

FIG. 19 illustrates an exemplary view of the user when wearing the virtual reality display. Through the virtual reality display, the user may see the patient simulator 12. A virtual display 300, a virtual C-arm 302 and optional additional information are displayed on the see-through screen of the virtual reality display, thereby creating a virtual reality experience for the user. The simulated medical images are displayed on the virtual display 300 along with an ECG graph.

Modifications and improvements to the above-described implementations of the present technology may become apparent to those skilled in the art. The foregoing description is intended to be exemplary rather than limiting.

What is claimed is:

1. A computer-implemented method for creating a training scenario to perform a percutaneous coronary intervention using an elongated instrument and a patient simulator, the computer-implemented method comprising:

receiving a desired position for a lesion;

receiving a desired value for at least one property of the lesion;

configuring a haptic feedback to be applied on the elongated instrument when received in the patient simulator based on the desired position for the lesion and the desired value for the properties of the lesion;

generating an electrocardiogram (ECG) graph outputting the ECG graph, the haptic feedback, the desired position and the desired value for the properties, wherein said generating the ECG graph comprises accessing a database comprising a plurality of predefined ECG graphs each having associated thereto a respective first lesion position and at least one respective first property value and selecting the ECG graph amongst the plurality of predefined ECG graphs based on the desired position and the desired value.

2. The computer-implemented method of claim 1, wherein said receiving the desired position comprises receiving a selection of the desired position amongst a predefined number of possible lesion positions.

3. The computer-implemented method of claim 1, wherein the at least one property of the lesion comprises at least one of a length of the lesion, an occlusion percentage, a Thrombolysis In Myocardial Infarction (TIMI) flow grade and an eccentricity of the lesion.

4. The computer-implemented method of claim 1, further comprising generating a patient description based on the desired position for the lesion and the desired value for the at least one property of the lesion and outputting the patient description.

5. The computer-implemented method of claim 4, wherein said generating the patient description comprises accessing the database further comprising a plurality of predefined patient descriptions each having associated thereto a respective second lesion position and at least one respective second property value and selecting the patient description amongst the plurality of predefined patient descriptions based on the desired position and the desired value.

6. A system for training a healthcare professional to perform a percutaneous coronary intervention, the system comprising:

a patient simulator configured for receiving a portion of an elongated instrument therein and applying a haptic feedback on the received portion of the elongated instrument; and a processing unit coupled to a memory, the processing unit being configured for:

allowing a trainer to define a position of a lesion and a value for at least one property of the lesion;

configuring the haptic feedback based on the position and properties of the lesion; and generating an electrocardiogram (ECG) graph and providing the ECG graph for display;

wherein said generating the ECG graph comprises accessing a database comprising a plurality of predefined ECG graphs each having associated thereto a respective first lesion position and at least one respective first property value and selecting the ECG graph amongst the plurality of predefined ECG graphs based on the defined position and the defined value.

7. The system of claim 6, wherein the processing unit being configured for allowing the trainer to select the position of the lesion amongst a predefined number of possible lesion positions.

8. The system of claim 6, wherein the at least one property of the lesion comprises at least one of a length of the lesion, an occlusion percentage, a Thrombolysis In Myocardial Infarction (TIMI) flow grade and an eccentricity of the lesion.

9. The system of claim 6, wherein the processing unit is further configured for generating a patient description based on the defined position for the lesion and the at least one property of the lesion and providing the patient description for display.

10. The system of claim 9, wherein said generating the patient description comprises accessing the database further comprising a plurality of predefined patient descriptions each having associated thereto a respective second lesion position and at least one respective second property value and selecting the patient description amongst the plurality of predefined patient descriptions based on the defined position and the defined value.

11. A computer-implemented method for training a healthcare professional to perform a percutaneous coronary intervention using an elongated instrument and a patient simulator, the computer-implemented method comprising:

independently receiving:

a selection of a desired position and a desired physical attribute for a first lesion; and a selection of a desired position and a desired physical attribute for a second lesion;

processing a detected position and motion of the elongated instrument within the patient simulator and the selected position and physical attribute of each of the first and second lesion, to determine properties of a haptic feedback; and providing control signals causing the patient simulator to mechanically impart to the elongated instrument the haptic feedback having the determined properties; and generating an electrocardiogram (ECG) graph and providing the ECG graph for display, wherein said generating the ECG graph comprises accessing a database comprising a plurality of predefined ECG graphs each having associated thereto a respective first position and a respective first physical attribute for the first lesion and the second lesion and selecting the ECG graph amongst the plurality of predefined ECG graphs based on the desired position and the desired physical attribute for the first lesion and the second lesion.

12. The computer-implemented method of claim 11, wherein the physical attribute comprises at least one of a length of the lesion, an occlusion percentage, a Thrombolysis In Myocardial Infarction (TIMI) flow grade and an eccentricity of the lesion.

13. The computer-implemented method of claim 11, wherein the haptic feedback comprises at least one of a pulling force, a pushing force and a rotation.

14. The computer-implemented method of claim 11, further comprising generating a patient description based on a desired position for the first lesion and the second lesion and a desired physical attribute for the first lesion and the second lesion and outputting the patient description.

15. The computer-implemented method of claim 14, wherein said generating the patient description comprises accessing the database further comprising a plurality of predefined patient descriptions each having associated thereto a respective second position for the first and second lesions and a respective second physical attribute for the first lesion and the second lesion and selecting the patient description amongst the plurality of predefined patient descriptions based on the desired position for the first lesion and the second lesion and the desired physical attribute for the first lesion and the second lesion.

16. A system for training a healthcare professional to perform a percutaneous coronary intervention using an elongated instrument and a patient simulator, the system comprising:

a processor; and a non-transitory storage medium operatively connected to the processor, the non-transitory storage medium comprising computer-readable instructions;

the processor, upon executing the computer-readable instructions, being configured for:

independently receiving:

a selection of a desired position and a desired physical attribute for a first lesion; and a selection of a desired position and a desired physical attribute for a second lesion;

processing a detected position and motion of the elongated instrument within the patient simulator and the selected position and physical attribute of each of the first and second lesion, to determine properties of a haptic feedback;

providing control signals causing the patient simulator to mechanically impart to the elongated instrument the haptic feedback having the determined properties; and generating an electrocardiogram (ECG) graph and providing the ECG graph for display, wherein said generating the ECG graph comprises accessing a database comprising a plurality of predefined ECG graphs each having associated thereto a respective first position and a respective first physical attribute for the first lesion and the second lesion and selecting the ECG graph amongst the plurality of predefined ECG graphs based on the desired position and the desired physical attribute for the first lesion and the second lesion.

17. The system of claim 16, wherein the physical attribute comprises at least one of a length of the lesion, an occlusion percentage, a Thrombolysis In Myocardial Infarction (TIMI) flow grade and an eccentricity of the lesion.

18. The system of claim 16, wherein the haptic feedback comprises at least one of a pulling force, a pushing force and a rotation.

19. The system of claim 16, wherein the processor is further configured for generating a patient description based on the desired position for the first lesion and the second lesion and the desired physical attribute for the first lesion and the second lesion and providing the patient description for display.

20. The system of claim 19, wherein the generating the patient description comprises accessing the database comprising a plurality of predefined patient descriptions each having associated thereto a respective second position for the first lesion and the second lesion and a respective second physical attribute for the first lesion and the second lesion and selecting the patient description amongst the plurality of predefined patient descriptions based on the desired position for the first lesion and the second lesion and the desired physical attribute for the first lesion and the second lesion.

* * * * *